(12) United States Patent
Miura et al.

(10) Patent No.: US 7,960,716 B2
(45) Date of Patent: Jun. 14, 2011

(54) FIELD EFFECT TRANSISTOR AND METHOD OF PRODUCING THE SAME

(75) Inventors: Daisuke Miura, Tokyo (JP); Tomonari Nakayama, Yokohama (JP); Toshinobu Ohnishi, Yokohama (JP); Makoto Kubota, Tokyo (JP); Akane Masumoto, Yokohama (JP); Satomi Sugiyama, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 322 days.

(21) Appl. No.: 10/571,688

(22) PCT Filed: Mar. 8, 2005

(86) PCT No.: PCT/JP2005/004407
§ 371 (c)(1),
(2), (4) Date: Sep. 4, 2008

(87) PCT Pub. No.: WO2005/086253
PCT Pub. Date: Sep. 15, 2005

(65) Prior Publication Data
US 2008/0308789 A1    Dec. 18, 2008

(30) Foreign Application Priority Data
Mar. 10, 2004    (JP) .................................. 2004-067440

(51) Int. Cl.
*H01L 51/30* (2006.01)
*H01L 51/40* (2006.01)

(52) U.S. Cl. ..................... 257/40; 438/99; 257/E51.006; 257/E51.041

(58) Field of Classification Search ..................... 257/40, 257/E51.001–E51.052; 438/99
See application file for complete search history.

(56) References Cited

U.S. PATENT DOCUMENTS

| | | | |
|---|---|---|---|
| 5,659,181 A | 8/1997 | Bridenbaugh et al. | 257/40 |
| 6,531,654 B2 | 3/2003 | Sugiyama et al. | 136/258 |
| 6,794,275 B2 | 9/2004 | Kondo et al. | 438/485 |
| 6,963,120 B2 | 11/2005 | Shiozaki et al. | 257/458 |
| 7,026,231 B2 | 4/2006 | Kubota et al. | 438/586 |
| 7,094,625 B2 | 8/2006 | Miura et al. | 438/99 |

(Continued)

FOREIGN PATENT DOCUMENTS

| | | |
|---|---|---|
| JP | 5-55568 | 3/1993 |
| JP | 5-190877 | 7/1993 |

(Continued)

OTHER PUBLICATIONS

Aramaki, S., et al. "Solution-Processible Organic Semiconductor For Transistor Applications: Tetrabenzoporphyrin." Appl. Phys. Lett., vol. 84, No. 12 (Mar. 22, 2004): pp. 2085-2087.*

Bao, Z., et al. "Silsesquioxane Resins as High-Performance Solution Processible Dielectric Materials for Organic Transistor Applications." Adv. Funct. Mater., vol. 12, No. 8 (Aug. 2002): pp. 526-531.*

(Continued)

*Primary Examiner* — Matthew W Such
(74) *Attorney, Agent, or Firm* — Fitzpatrick, Cella, Harper & Scinto

(57) ABSTRACT

An object of the present invention is to provide a field effect transistor showing high field-effect mobility and a high ON/OFF ratio, which can be produced simply by using a porphyrin compound with excellent crystallinity and orientation. The field effect transistor according to the present invention transistor contains at least an organic semiconductor layer, wherein the organic semiconductor layer contains at least a porphyrin compound and has a maximum diffraction intensity $I_1$ in a Bragg angle (2θ) range of 9.9° to 10.4° stronger than a maximum diffraction intensity $I_2$ in a Bragg angle (2θ) range of 23.0° to 26.0° in X-ray diffraction using CuKα radiation.

11 Claims, 5 Drawing Sheets

U.S. PATENT DOCUMENTS

| | | | |
|---|---|---|---|
| 7,140,321 B2 | 11/2006 | Nakayama et al. | 118/723 |
| 2003/0226996 A1* | 12/2003 | Aramaki et al. | 252/62.3 Q |
| 2004/0149330 A1 | 8/2004 | Sugiyama et al. | 136/249 |
| 2005/0202348 A1 | 9/2005 | Nakayama et al. | 430/311 |
| 2006/0081880 A1 | 4/2006 | Miyazaki et al. | 257/200 |
| 2006/0113523 A1* | 6/2006 | Kubota et al. | 257/40 |
| 2006/0145141 A1 | 7/2006 | Miura et al. | 257/40 |
| 2006/0214159 A1 | 9/2006 | Nakayama et al. | 257/40 |
| 2007/0012914 A1 | 1/2007 | Miura et al. | 257/40 |
| 2007/0051947 A1 | 3/2007 | Nakayama et al. | 257/40 |
| 2007/0085072 A1 | 4/2007 | Masumoto et al. | 257/40 |

FOREIGN PATENT DOCUMENTS

| | | |
|---|---|---|
| JP | 8-264805 | 10/1996 |
| JP | 2001-94107 | 4/2001 |
| JP | 2003-304014 | 10/2003 |
| JP | 2004-6750 | 1/2004 |
| WO | WO 2004091001 A1 * | 10/2004 |

OTHER PUBLICATIONS

A. R. Brown, et al., "Precursor route pentacene metal-insulator-semiconductor field-effect transistors", Journal of Applied Physics, vol. 79, No. 4, Feb. 15, 1996, pp. 2136-2138.

Christos D. Dimitrakopoulos, et al., "Organic Thin Film Transistors for Large Area Electronics", Advanced Materials, vol. 14, No. 2, Jan. 16, 2002, pp. 99-117.

Peter T. Herwig, et al., "A Soluble Pentacene Precursor: Synthesis, Solid-State Conversion into Pentacene and Application in a Field-Effect Transistor", Advanced Materials, vol. 11, No. 6, 1999, pp. 480-483.

T. Akiyama, "Synthesis of .pai.-system-expanded compounds using Diels-Alder reactions", Proceedings of the 81st Annual Spring Meeting of the Chemical Society of Japan, 2002, vol. II, p. 990, 2F9-14. (with translation).

* cited by examiner

FIELD EFFECT TRANSISTOR AND METHOD OF PRODUCING THE SAME

TECHNICAL FIELD

The present invention relates to a field effect transistor, and a method of producing the same.

BACKGROUND ART

The development of thin-film transistors employing an organic semiconductor gradually began to become more active in the latter half of the 1980s, and has in recent years reached the stage where the characteristics of a thin-film transistor employing an organic semiconductor exceed the characteristics of a thin-film transistor of amorphous silicon for basic performance. Organic materials are easily processed and generally have a high affinity with a plastic substrate on which a thin-film field effect transistor (FET) is usually formed. Therefore, the use of an organic material as a semiconductor layer in a thin-film device is desirable. The organic semiconductor include acenes such as pentacene and tetracene, disclosed by Japanese Patent Application Laid-Open No. H5-55568; phthalocyanines including lead phthalocyanine, and low-molecular-weight compounds such as perylene and tetracarboxylic acid derivatives thereof, disclosed by Japanese Patent Application Laid-Open No. H5-190877; and aromatic oligomers typified by thiophene hexamers referred to as α-thienyl or sexithiophene, as well as high-molecular-weight compounds such as polythiophene, polythienylenevinylene and poly-p-phenylenevinylene, disclosed by Japanese Patent Application Laid-Open No. H8-264805. (Many of these compounds are also disclosed by "Advanced Materials", Vol. 2, p. 99, 2002.)

Properties such as non-linear optical properties, electrical conductivity and semiconductivity, which are required for using the above compounds as the semiconductor layer in a device, depend not only on the purity of the compounds but also largely on crystallinity and orientation of the compounds. CuKα X-ray diffraction of a vapor-deposited film of a compound having an extended π-conjugation, for example pentacene, has been reported in terms of Bragg angle 2θ (Japanese Patent Application Laid-Open No. 2001-94107). In addition to this report, there are many other reports of field effect transistors that use a vapor-deposited film of pentacene in the semiconductor layer, whereby it is known that the transistors show high field-effect mobility because of the excellent crystallinity and orientation of the vapor-deposited film of pentacene. However, because pentacene is unstable in air and tends to be oxidized and easily degraded, an apparatus for forming a film of pentacene by vacuum deposition was required, which is a problem of increasing the costs of the transistors using a film of pentacene.

On the other hand, a field effect transistor has also been reported which was produced by a method of coating with a low-molecular-weight compound and converting the compound to an organic semiconductor compound by heating. In this method, although tetrachlorobenzene is eliminated by the heating, since the boiling point of tetrachlorobenzene is high, it remains in the system at normal pressure, thus hindering the crystallinity of the pentacene (J. Appl. Phys. Vol. 79, p. 2136, 1996). In addition, a method of converting to pentacene by the elimination of ethylene has been reported, and this method was pointed out that the elimination of ethylene is difficult to carry out and therefore a precursor in this case is unsuitable ("Advanced Materials", Vol. 11, p. 480, 1999).

It has also been reported that it is possible to utilize tetrabenzoporphyrin obtained by heating at 210° C. a porphyrin formed by ring-shrinking a bulky bicyclo[2.2.2]octadiene skeleton as an organic semiconductor (Proceedings of the 81st Annual Spring Meeting of the Chemical Society of Japan, 2002, II, p. 990, 2F9-14; Japanese Patent Application Laid-Open No. 2003-304014; Japanese Patent Application Laid-Open No. 2004-6750). However, in this case it is thought that optimum crystal orientation for carrier movement is not achieved, whereby sufficient characteristics were unable to be obtained.

As described above, conventionally field effect transistors employing an organic semiconductor compound have been produced with a semiconductor layer having crystallinity and orientation which is formed by a process such as vacuum film formation. However, as the typical example, acenes have the problem of being likely to be degraded by oxidation. Also, the above conventional simple technique employing a coating method has a problem of not producing a film with crystallinity and orientation showing sufficient characteristics.

DISCLOSURE OF INVENTION

The field effect transistor of the present invention includes at least an organic semiconductor layer, wherein the organic semiconductor layer contains at least a porphyrin compound and has a maximum diffraction intensity $I_1$ in a Bragg angle (2θ) range of 9.9° to 10.4° stronger than a maximum diffraction intensity $I_2$ in a Bragg angle (2θ) range of 23.0° to 26.0° in X-ray diffraction using CuKα radiation.

In the field effect transistor of the present invention, the ratio $I_1/I_2$ of the maximum diffraction intensity $I_1$ and the maximum diffraction intensity $I_2$ is preferably 2 or more.

In the field effect transistor of the present invention, the porphyrin compound is preferably tetrabenzoporphyrin.

In the field effect transistor of the present invention, the porphyrin compound is preferably a metal-free porphyrin.

In the field effect transistor of the present invention, the porphyrin compound is preferably formed by heating a precursor having a bicyclo[2.2.2]octadiene skeleton.

The method of the present invention of producing a field effect transistor including at least an organic semiconductor layer, including the steps of heating a precursor having a bicyclo[2.2.2]octadiene skeleton to form a porphyrin compound, and using at least the porphyrin compound to form at least the organic semiconductor layer, wherein the organic semiconductor layer has a maximum diffraction intensity $I_1$ in a Bragg angle (2θ) range of 9.9° to 10.4° stronger than a maximum diffraction intensity $I_2$ in a Bragg angle (2θ) range of 23.0° to 26.0° in X-ray diffraction using CuKα radiation.

In the method of present invention of producing a field effect transistor, it is preferable that the porphyrin compound is used to form the organic semiconductor layer so that the ratio $I_1/I_2$ of the maximum diffraction intensity $I_1$ to the maximum diffraction intensity $I_2$ is 2 or more.

In the method of the present invention of producing a field effect transistor, tetrabenzoporphyrin is preferably used as the porphyrin compound.

In the method of the present invention of producing a field effect transistor, a metal-free porphyrin is preferably used as the porphyrin compound.

The field effect transistor according to the present invention can be simply produced and has excellent crystallinity and orientation, and therefore the field effect transistor of the present invention shows high field-effect mobility and a high ON/OFF ratio.

BEST MODE FOR CARRYING OUT THE INVENTION

Figure 1:
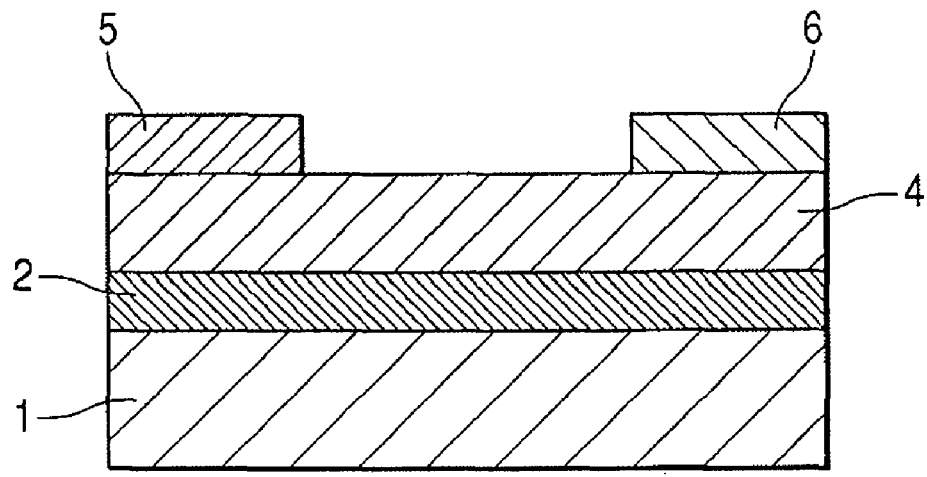
FIG. 1 is an expanded schematic view showing a part of a field effect transistor according to the present invention.

The field effect transistor according to the present invention is characterized by employing an organic semiconductor layer which contains at least a porphyrin compound and has the maximum diffraction intensity $I_1$ in a Bragg angle (2θ) range of 9.9° to 10.4° stronger than the maximum diffraction intensity $I_2$ in a Bragg angle (2θ) range of 23.0° to 26.0° in X-ray diffraction using CuKα.

Although the porphyrin compound is not particularly limited as long as it has at least a porphyrin skeleton in its molecule, the porphyrin compound is preferably tetrabenzoporphyrin represented by the following general formula (1), and more preferably tetrabenzoporphyrin of the general formula (1) obtained by coating a solvent solution containing a compound of the following general formula (2) onto a substrate then heating.

General formula (1)

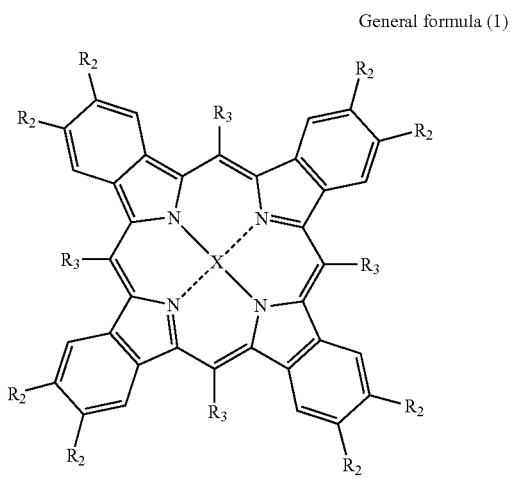

wherein each $R_2$ independently denote at least one selected from a hydrogen atom, a halogen atom, a hydroxyl group, or a alkyl group, an oxyalkyl group, a thioalkyl group, or an alkyl ester group, each group having 1 to 12 carbon atoms, and $R_2$ may be the same or different; each $R_3$ is selected from a hydrogen atom or an aryl group which may have a substituent group, and $R_3$ may be the same or different; and X denotes a hydrogen atom or a metal atom.

General formula (2)

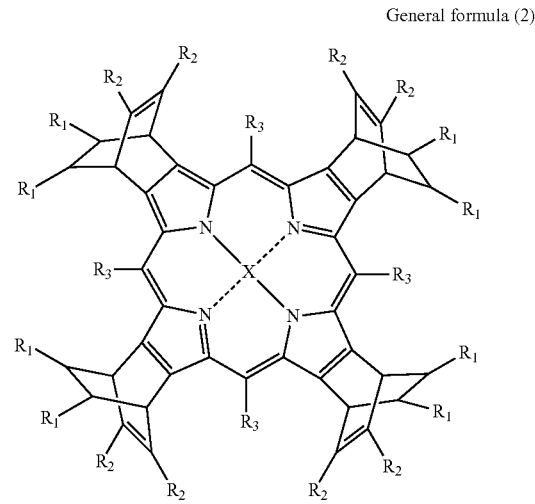

wherein each of $R_1$ and $R_2$ independently denote at least one selected from a hydrogen atom, a halogen atom, a hydroxyl group, or an alkyl group, an oxyalkyl group, a thioalkyl group, or an alkyl ester group, each group having 1 to 12 carbon atoms, and $R_1$ and $R_2$ may be the same or different; each $R_3$ is selected from a hydrogen atom or an aryl group which may have a substituent group, and $R_3$ may be the same or different; X denotes a hydrogen atom or a metal atom.

According to the present invention, the organic semiconductor layer may contain a mixture of 2 or more porphyrin compounds of different center metals, or 2 or more porphyrin compounds having different structures. Preferably, the organic semiconductor layer contains at least a metal-free tetrabenzoporphyrin.

The present inventors focused their attention on crystallinity and orientation of the porphyrin compound as represented by the general formula (1), whereby as a result of continued investigation they found that a field effect transistor having stronger diffraction on the low-angle side than the high-angle side in CuKα X-ray diffraction shows a higher field-effect mobility than that of a field effect transistor having no such diffraction.

Based on the above finding, further intensive research was carried out to arrive at the present invention, that is, a field effect transistor including at least an organic semiconductor layer, wherein the organic semiconductor layer contains at least a porphyrin compound and has the maximum diffraction intensity $I_1$ in a Bragg angle (2θ) range of 9.9° to 10.4° stronger than the maximum diffraction intensity $I_2$ in a Bragg angle (2θ) range of 23.0° to 26.0° in X-ray diffraction using CuKα radiation, and wherein the field effect transistor shows a high field-effect mobility and a high On/Off ratio. More preferably, the maximum diffraction intensity ratio of $I_1/I_2$ is 2 or more.

Although the reason for the above is not clear, it is known that field effect transistors show a higher field-effect mobility by orienting the molecular plane of the organic molecules having an extended π-conjugated system in a direction perpendicular to the substrate.

The present inventors surmise that the diffraction seen on the low-angle side of the organic semiconductor layer according to the present invention indicates that the organic semiconductor layer has a structure of orienting the molecular plane of the organic compound having a conjugated plane in a direction perpendicular to the substrate.

The X-ray diffraction measurement in the present invention was carried out under the following conditions.
Apparatus: RAD-RX wide angle X-ray diffraction apparatus manufactured by Rigaku Denki Corporation
X-ray tube: Cu
Tube voltage: 50 KV
Tube current: 150 mA
Scan method: 2θ/θ scan
Scan rate: 2 deg./min.
Sampling interval: 0.02 deg.
Total time: 1 s
Total repetitions: 14 times
Measurement temperature: room temperature (20° C.)
A plane at θ=0° was set on the substrate.

Each of the diffraction intensities $I_1$ and $I_2$ in the present invention denotes the value from which a baseline intensity has been subtracted from the top of the diffraction peak.

In the present invention the shape of the X-ray diffraction peak may slightly differ depending on the conditions during production. Further, in some cases the peak tip may be split.

The present invention will be now explained in more detail.

In the present invention, the substituent $R_1$ bonded to the bicyclooctadiene ring of the bicycloporphyrin compound (hereinafter referred to as "bicyclo compound") represented by the general formula (2) is eliminated by heat treatment in the form of $R_1$—CH=CH—$R_1$ during conversion to the tetrabenzoporphyrin compound (hereinafter referred to as "benzo compound") represented by the general formula (1). Therefore, each $R_1$ may be independently at least one selected from a hydrogen atom, a halogen atom, a hydroxyl group, or an alkyl group, an oxyalkyl group, a thioalkyl group or an alkyl ester group, each group having 1 to 12 carbon atoms, or may be a combination of two or more thereof. If the number of carbon atoms exceeds 12, the molecular weight of a component to be eliminated increases and the component to be eliminated remains in a benzo compound film, resulting in inadequate semiconductor characteristics. $R_1$ is most preferably a hydrogen atom.

The substituent $R_2$ of the bicyclo compound represented by the general formula (2) remains as a substituent on the benzo compound represented by the general formula (1) obtained after heat treatment. Therefore, the substituent $R_2$ influences the orientation of the benzo compound. Each $R_2$ may be independently at least one selected from a hydrogen atom, a halogen atom, a hydroxyl group, or an alkyl group, an oxyalkyl group, a thioalkyl group or an alkyl ester group, each group having 1 to 12 carbon atoms, or may be a combination of two or more thereof. If the number of carbon atoms of $R_2$ exceeds 12, the existence ratio of porphyrin ring to the whole molecule decreases to thereby make orientation of the porphyrin rings more difficult and result in inadequate semiconductor characteristics. Most preferably, $R_2$ is a hydrogen atom, whereby the stacking of porphyrin rings occurs more easily to enhance the crystallinity of a film.

X denotes a hydrogen atom or a metal atom. Examples of X are H, metals such as Cu, Zn, Ni, Co, Mg, and Fe, and atomic groups such as AlCl, TiO, FeCl and $SiCl_2$. Although X is not particularly limited, X is particularly preferably a hydrogen atom or a copper atom. In the examples according to the present invention, X is preferably a hydrogen atom.

Preferable examples of the method for forming the organic semiconductor layer include a method in which the bicyclo compound is dissolved in an organic solvent, coated on a substrate and then heated to obtain a crystallized film of the benzo compound.

The organic solvent to be used for dissolving the bicyclo compound is not particularly limited, provided that it the organic solvent neither reacts with the porphyrin compound nor precipitates the same. Further, two or more solvents may be mixed for use. Halogenated organic solvents are preferably used in consideration of smoothness of the surface of a coating film and the uniformity of a film thickness. Examples of halogenated organic solvents include chloroform, methylene chloride, dichloroethane, chlorobenzene, and 1,2-dichloroethylene. The solution may be arbitrarily adjusted to any concentration depending on a desired film thickness, but the concentration is preferably from 0.01 to 5% by weight.

Examples of the coating method include conventional coating methods, such as a spin coating method, a casting method, a spray coating method, a doctor blade method, a die-coating method, a dipping method, a printing method, an ink jet method and a dropping method. Among these methods, spin coating, dipping, spray coating and ink jet method are preferable because these methods can control the coating amount to form a film having a desired thickness.

Further, it is desirable to preliminarily filter the solution through a membrane filter in order to prevent the mixture of dirt and the like into a semiconductor layer. This is because insolubles and the mixed dirt from outside hinder uniform orientation, thereby resulting in an increase in the OFF current and a reduction in the ON/OFF ratio. The coating film of the benzo compound may also be preliminarily dried at 100° C. or lower.

The coated film of the bicyclo compound is subjected to a retro Diels-Alder reaction by heating to be converted to a benzo compound with the elimination of $R_1$—CH=CH—$R_1$. At the same time of formation of the benzo compound, crystal growth is caused by the stacking of porphyrin rings, thereby resulting in a crystallized film of the benzo compound. Although the elimination reaction occurs at 140° C. or higher, the preferable heating temperature for obtaining a higher field-effect mobility is from 150 to 280° C. and preferably in the range from 170 to 230° C. An adequate crystallized film by crystal growth cannot be obtained at a heating temperature of lower than 150°, and cracks will occur due to an abrupt shrinkage of the film when the heating temperature exceeds 280° C.

The heating method is not particularly limited, and heating may be carried out on a hot plate, in a hot air-circulating oven or in a vacuum oven. However, to obtain uniform orientation, instantaneous heating using a hot plate is preferable.

Further, in order to obtain higher crystallinity, the coating film before heat treatment is preferably subjected to a rubbing treatment in which the coating film is lightly rubbed with a cloth or the like. The cloth for use in the rubbing treatment includes, but is not limited to, rayon, cotton or silk.

The film thickness of the organic semiconductor layer using the oriented film of the benzo compound obtained by these operations is from 10 to 200 nm, and preferably from 20 to 100 nm. The term "film thickness" as used here refers to the average value of the film thickness values measured using a surface roughness measuring device, a step difference measuring device or the like.

It is also thought that the same effects as those of the present invention can be achieved even if the porphyrin compound used in the present invention is replaced with another general organic semiconductor compound such as phthalocyanine or the like.

Although the organic film obtained in the present invention is most preferably used in a field effect transistor, the organic film may also be applied to other devices.

FIGS. 1 to 4 are expanded schematic views showing a part of the field effect transistor according to the present invention. The field effect transistor according to the present invention is composed of a gate electrode 1, a gate insulating layer 2, an interface layer 3, an organic semiconductor substrate 4, a source electrode 5, and a drain electrode 6.

Materials for the gate electrode, source electrode and drain electrode are not particularly limited, provided that they are electrically conductive materials, and include platinum, gold, silver, nickel, chromium, copper, iron, tin, antimony, lead, tantalum, indium, aluminum, zinc, magnesium and alloys thereof; electrically conductive metal oxides such as indium-tin oxide; and inorganic and organic semiconductors having a conductivity increased by doping or the like, for example, a silicon single-crystal, polysilicon, amorphous silicon, germanium, graphite, polyacetylene, polyparaphenylene, polythiophene, polypyrrole, polyaniline, polythienylenevinylene and polyparaphenylenevinylene. Methods of forming the electrodes include sputtering, vapor deposition, a printing method using a solution or a paste or an ink jet method. Further, preferable electrode materials among the above list are those having a low electrical resistance at the contact surface with the semiconductor layer.

For the gate insulating layer, any gate insulating layer may be used, provided that a solution of the bicyclo compound can be uniformly coated thereon, but those having a high dielectric constant and low conductivity are preferred. Examples thereof include inorganic oxides and nitrides such as silicon oxide, silicon nitride, aluminum oxide, titanium oxide and tantalum oxide; and organic polymers such as polyacrylates, polymethacrylates, polyethylene terephthalate, polyimides, polyethers and siloxane-containing polymers. In addition, among the above insulating materials, those having a high surface-smoothness are preferred.

In order to improve the uniformity of the coating film formed from the bicyclo compound solution on the insulating layer, and to make the orientation of the film of the benzo compound uniform by heating, it is also possible to modify only the surface of the insulating film. The surface modifying method includes a dry treatment using ozone, plasma or a hexamethyldisilazane gas, and a wet treatment using a solution prepared by dissolving tetraalkoxysilane, trichlorosilane, a surfactant or the like in an organic solvent.

The field effect transistor structure according to the present invention may be either a top-contact electrode type or a bottom-contact electrode type, or the like. Further, the transistor structure configuration may be a horizontal type or a vertical type.

Synthesis examples and Examples will be now described. However, the present invention is not limited to these Synthesis examples and Examples.

SYNTHESIS EXAMPLE

Step 1-1

A mixed solution of 3.16 g (39.5 mmol) of 1,3-cyclohexadiene, 10.5 g (34.1 mmol) of trans-1,2-bis(phenylsulfonyl)ethylene and 200 ml of toluene was refluxed for 7 hours, then cooled and concentrated under reduced pressure to give a reaction mixture. This reaction crude product was made to recrystallize, thereby giving 5,6-bis(phenylsulfonyl)-bicyclo[2.2.2]octa-2-ene (13.8 g, 35.6 mmol, yield 90%).

Step 1-2

The reaction system of a mixed solution of 7.76 g (20 mmol) of the obtained 5,6-bis(phenylsulfonyl)-bicyclo[2.2.2]octa-2-ene and 50 ml of anhydrous tetrahydrofuran was purged with a nitrogen gas, and 2.425 (22 mmol) of ethyl isocyanoacetate was added to the system, which was then cooled to 0° C. After dropping potassium t-butoxide (50 ml/1M THF solution) over 2 hours, the solution was stirred for 3 hours. After the reaction was finished, dilute hydrochloric acid was added to the solution. The reaction mixture was then washed in turn with saturated aqueous sodium bicarbonate, distilled water and saturated saline, and dried over anhydrous sodium sulfate. The resulting product was purified using silica gel column chromatography (chloroform) to give ethyl-4,7-dihydro-4,7-ethano-2H-isoindole-1-carboxylate (3.5 g, 16 mmol, yield 80%).

Step 1-3

Under an argon atmosphere, a mixed solution of 0.42 g (1.92 mmol) of the obtained ethyl-4,7-dihydro-4,7-ethano-2H-isoindole-1-carboxylate and 50 ml of anhydrous THF was cooled to 0° C., and 0.228 g (6 mmol) of lithium aluminum hydride was added to the solution and the solution was stirred for 2 hours. Then THF was removed. The residue was extracted with chloroform, and the extract was washed in turn with saturated aqueous sodium bicarbonate, distilled water and saturated saline, and dried over anhydrous sodium sulfate. This reaction solution was filtered, purged with an argon gas and shielded from light, and 10 mg of p-toluenesulfonic acid was added to the solution and the mixture solution was stirred for 12 hours at room temperature. Then, 0.11 g of p-chloranil was added to the reaction solution and the solution was stirred for 12 hours at room temperature. The reaction solution was washed in turn with saturated aqueous sodium bicarbonate, distilled water and saturated saline, and dried over anhydrous sodium sulfate. After the solution was concentrated, the solution was subjected to alumina column chromatography (chloroform) and recrystallization (chloroform/methanol) to give a metal-free tetrabicyclo compound (0.060 g, 0.097 mmol, yield 20%) represented by general formula (3).

General formula (3)

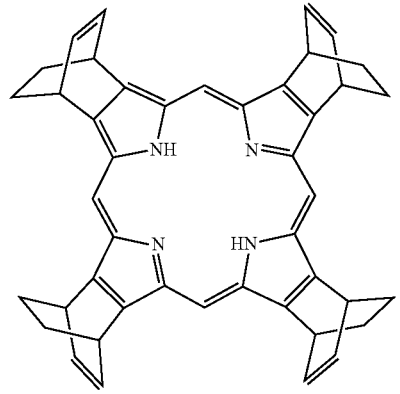

Step 1-4

0.02 g (0.032 mmol) of the obtained metal-free tetrabicyclo compound and 0.019 g (0.1 mmol) of copper (II) acetate monohydrate in 30 ml chloroform solution were stirred for 3 hours at room temperature. The reaction solution was washed with distilled water and saturated saline, then dried over anhydrous sodium sulfate. After the solution was concentrated, a tetrabicyclo copper complex (0.022 g, yield 100%) was obtained by recrystallization using chloroform/methanol.
(Preparation of Resin Solution a)

A 1% by weight concentration solution was prepared by dissolving 1.0 g of commercially available flaked methylsilsesquioxane (MSQ) (manufactured by Showa Denko K.K.; product name: GR650) in a mixed solvent of 49.5 g of ethanol and 49.5 g of 1-butanol. This solution was used as resin solution a.

Example 1

FIG. 1 shows the structure of a field effect transistor according to the present example.

First, a highly-doped N-type silicon substrate was provided as a gate electrode 1. A silicon oxide film with a thickness of 5,000 angstroms obtained by thermally oxidizing the surface layer of the silicon substrate was used as a gate insulating layer 2. 1% by weight of a mixture of the metal-free tetrabicyclo compound and tetrabicyclo copper complex synthesized in Synthesis example 1 (weight ratio 1:1) in chloroform solution was coated onto the substrate by spin coating (revolution speed 1000 rpm). The substrate was heated to 220° C. to form an organic semiconductor layer 4. A gold source electrode 5 and a gold drain electrode 6 were formed using a mask. The electrode formation conditions were as follows. The degree of vacuum in the vapor-deposition apparatus chamber was $1 \times 10^{-6}$ torr, the substrate temperature was room temperature and the film thickness was 100 nm.

A field effect transistor with a channel length of 50 µm and a channel width of 3 mm was produced according to the above procedure. The $V_d$-$I_d$ and $V_g$-$I_d$ curves of the produced transistor were measured using a Parameter Analyzer 4156C (trade name) made by Agilent Inc.

Mobility µ (cm$^2$/Vs) was calculated according to the following equation (1).

$$I_d = \mu (CiW/2L)(V_g - V_{th})^2 \quad \text{(Equation 1)}$$

wherein Ci denotes capacitance (F/cm$^2$) per unit area of the gate insulating film; W and L respectively denote a channel width (mm) and a channel length (µm) shown in the example; and $I_d$, $V_g$ and $V_{th}$ respectively denote a drain current (A), a gate voltage (V) and a threshold voltage (V). Further, the ratio of $I_d$ for $V_g$=−80 V to $I_d$ for $V_g$=0 V at $V_d$=−80 V was defined as an ON/OFF ratio.

CuKα X-ray diffraction of the transistor substrate produced under the above-described conditions was carried out.

Figure 6:
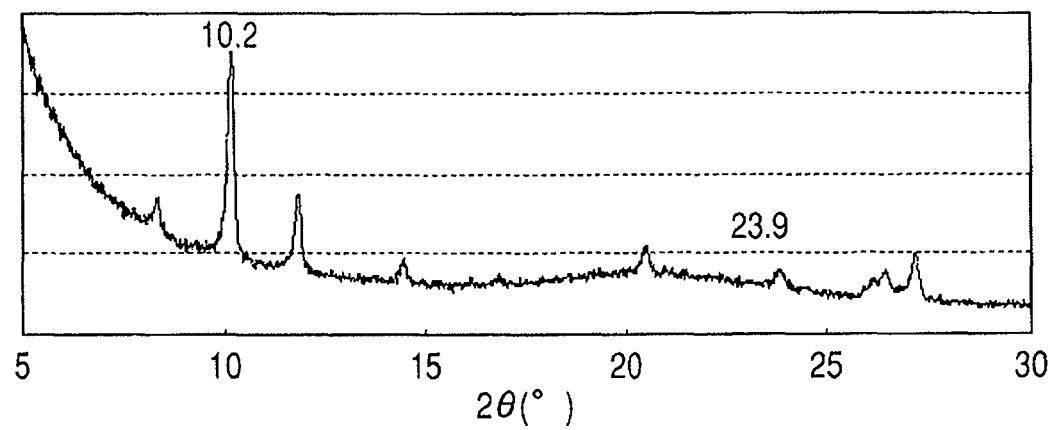
FIG. 6 is an X-ray diffraction pattern of the transistor substrate obtained in Example 1 of the present invention.

The results are shown in Table 1 and FIG. 6.

Example 2

Figure 2:
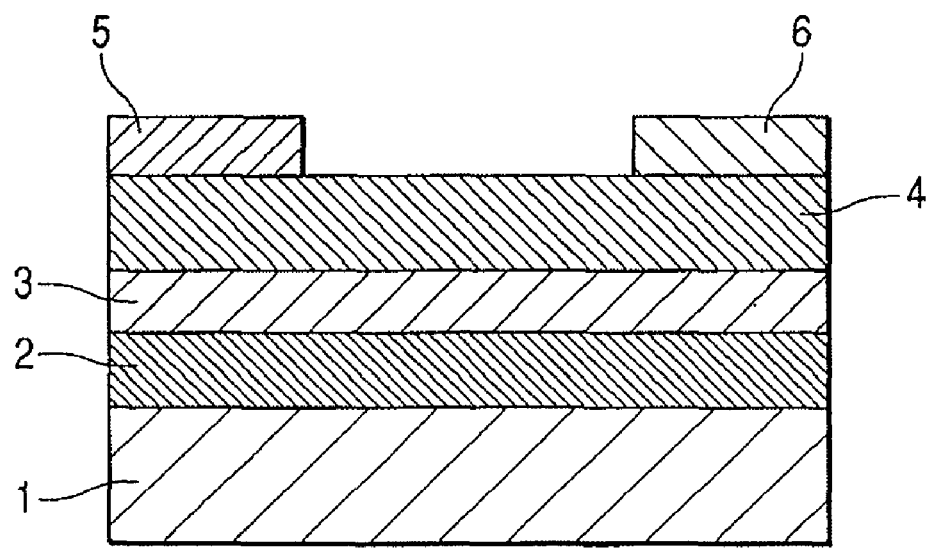
FIG. 2 is an expanded schematic view showing a part of a field effect transistor according to the present invention.

FIG. 2 shows the structure of a field effect transistor according to the present example. First, a highly-doped N-type silicon substrate was provided as a gate electrode 1. A silicon oxide film with a thickness of 5,000 angstroms obtained by thermally oxidizing the surface layer of the silicon substrate was used as a gate insulating layer 2. The resin solution a was then coated onto the surface of the insulating layer by spin coating (revolution speed 5000 rpm). Next, the coated film was transferred to a hot plate, and heated at 100° C. for 5 minutes and at 200° C. for 20 minutes. The film thickness was 50 nm as measured using a stylus-type step difference measuring device. This film served as an interface layer 3. 1% by weight of the metal-free tetrabicyclo compound synthesized in Synthesis example 1 in chloroform solution was coated onto the substrate by spin coating (revolution speed 1000 rpm). The substrate was heated to 200° C. to form an organic semiconductor layer 4. A gold source electrode 5 and a gold drain electrode 6 were then produced using a mask under the conditions as described above.

A field effect transistor with a channel length of 50 µm and a channel width of 3 mm was produced according to the above procedure and evaluated for its electrical characteristics. CuKα X-ray diffraction of the transistor substrate produced under the above-described conditions was also carried out.

Figure 5:
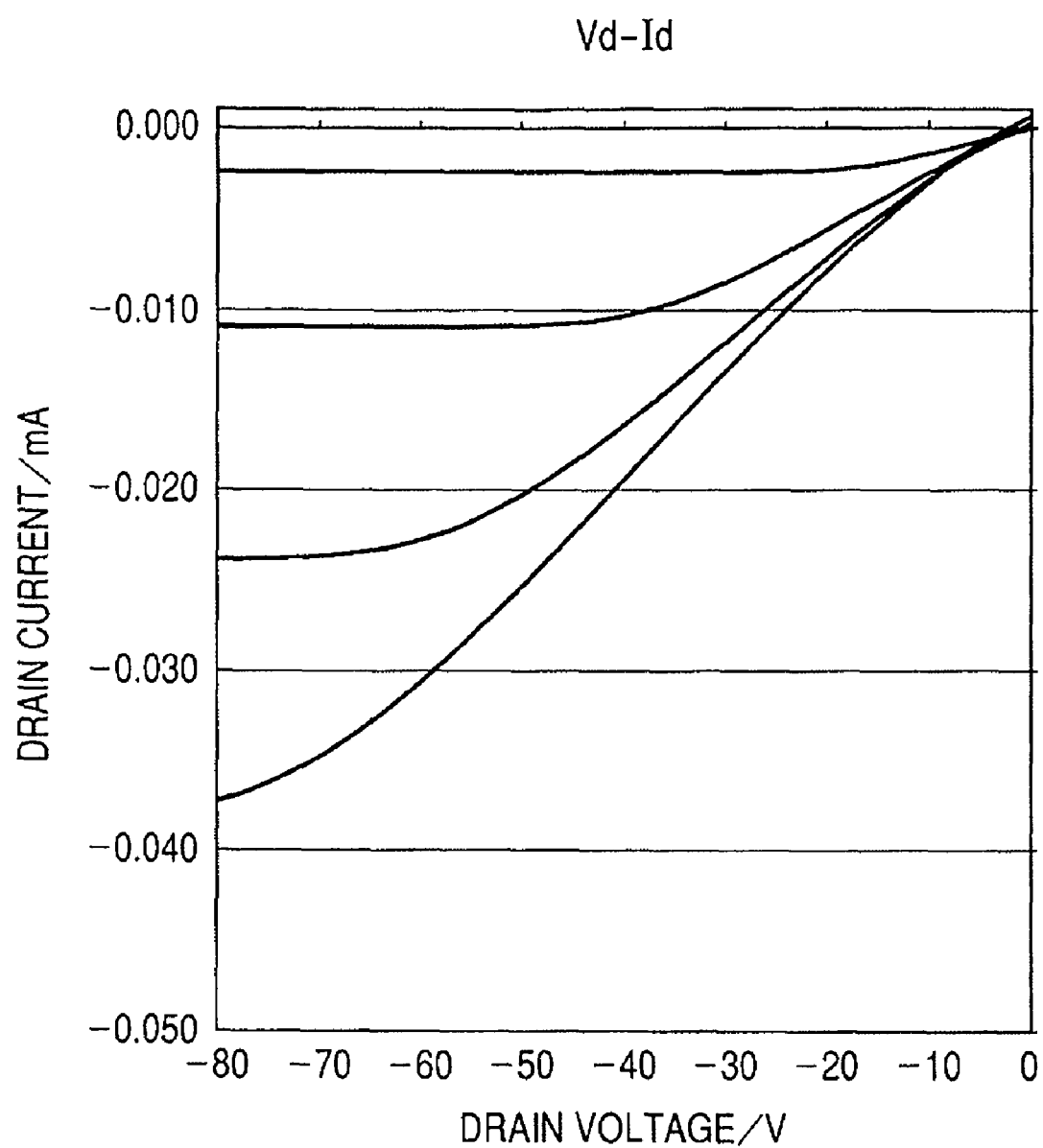
FIG. 5 is a graph showing the electrical characteristics of the field effect transistor produced in Example 2 of the present invention.
Figure 7:
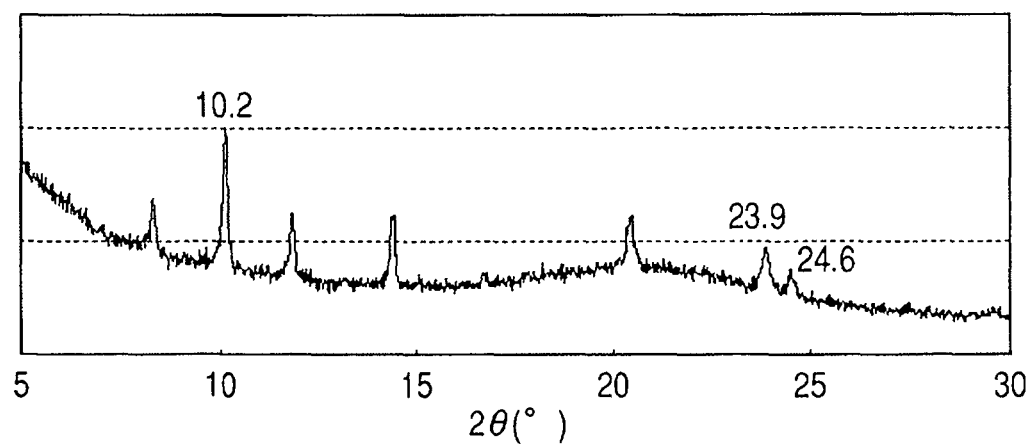
FIG. 7 is an X-ray diffraction pattern of the transistor substrate obtained in Example 2 of the present invention.

These results are shown in Table 1 and FIGS. 5 and 7. FIG. 5 shows the results of measurement carried out with a $V_d$-$I_d$ curve at $V_g$=0 to −80 (step: 20 V).

Example 3

Figure 3:
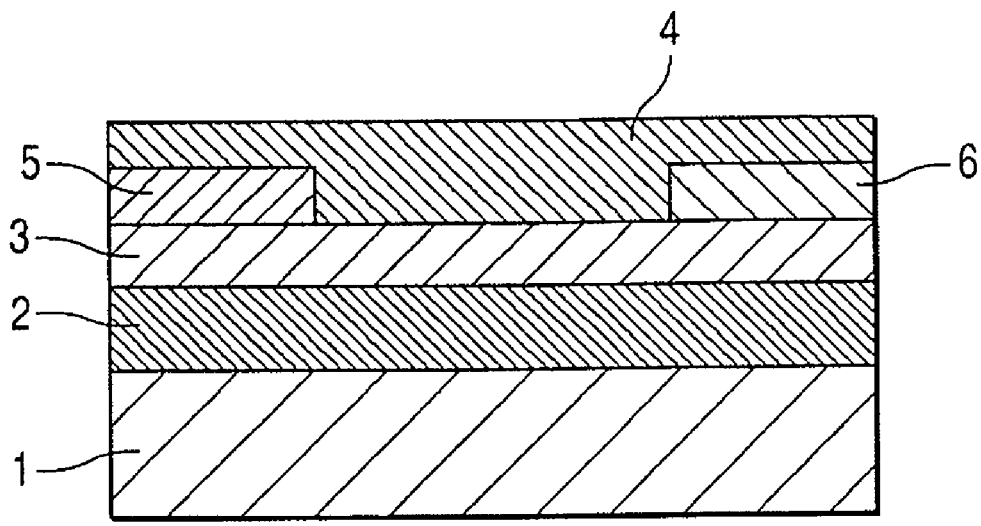
FIG. 3 is an expanded schematic view showing a part of a field effect transistor according to the present invention.

FIG. 3 shows the structure of a field effect transistor according to the present example. First, a highly-doped N-type silicon substrate was provided as a gate electrode 1. A silicon oxide film with a thickness of 5,000 angstroms obtained by thermally oxidizing the surface layer of the silicon substrate was used as a gate insulating layer 2. A resin solution a was then coated onto the surface of the insulating layer by spin coating (revolution speed 5000 rpm). Next, the coated film was transferred to a hot plate, and heated at 100° C. for 5 minutes and at 200° C. for 20 minutes. The film thickness was 50 nm as measured using a stylus-type step difference measuring device. This film served as an interface layer 3. A gold source electrode 5 and a gold drain electrode 6 were then formed using a mask under the conditions as described above. 1% by weight of the metal-free tetrabicyclo compound synthesized in Synthesis example 1 in chloroform solution was coated onto the substrate by spin coating (revolution speed 1000 rpm). The substrate was heated to 220° C. to form an organic semiconductor layer 4.

A field effect transistor with a channel length of 50 µm and a channel width of 3 mm was produced according to the above procedure and evaluated for its electrical characteristics. CuKα X-ray diffraction of the transistor substrate produced under the above-described conditions was also carried out.

Figure 8:
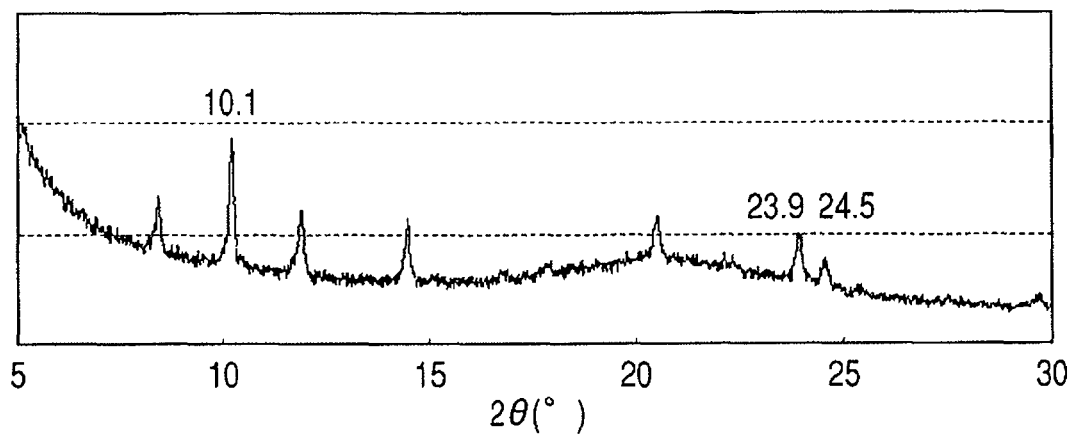
FIG. 8 is an X-ray diffraction pattern of the transistor substrate obtained in Example 3 of the present invention.

These results are shown in Table 1 and FIG. 8.

Comparative Example 1

Figure 4:
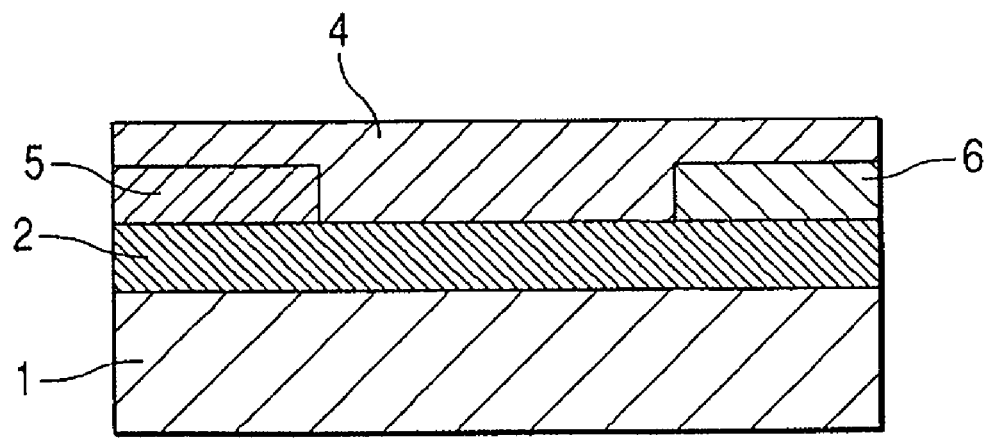
FIG. 4 is an expanded schematic view showing a part of a field effect transistor according to the present invention.

FIG. 4 shows the structure of a field effect transistor according to the present comparative example.

First, a highly-doped N-type silicon substrate was provided as a gate electrode 1. A silicon oxide film with a thickness of 5,000 angstroms obtained by thermally oxidizing the surface layer of the silicon substrate was used as a gate insulating layer 2. Chromium and gold were vapor-deposited in that order onto the gate insulating layer, and a comb-type structure source electrode 5 and drain electrode 6 having L=50 µm and W=10.26 mm were formed using a conventional optical lithography process. 0.8% by weight of the metal-free tetrabicyclo compound synthesized in Synthesis example 1 in chloroform solution was coated onto the substrate by spin coating (revolution speed 1000 rpm). The substrate was heated to 190° C. to form an organic semiconductor layer 4.

A field effect transistor was prepared according to the above procedure and evaluated for its electrical characteristics. CuKα X-ray diffraction of the transistor substrate produced under the above-described conditions was also carried out.

Figure 9:
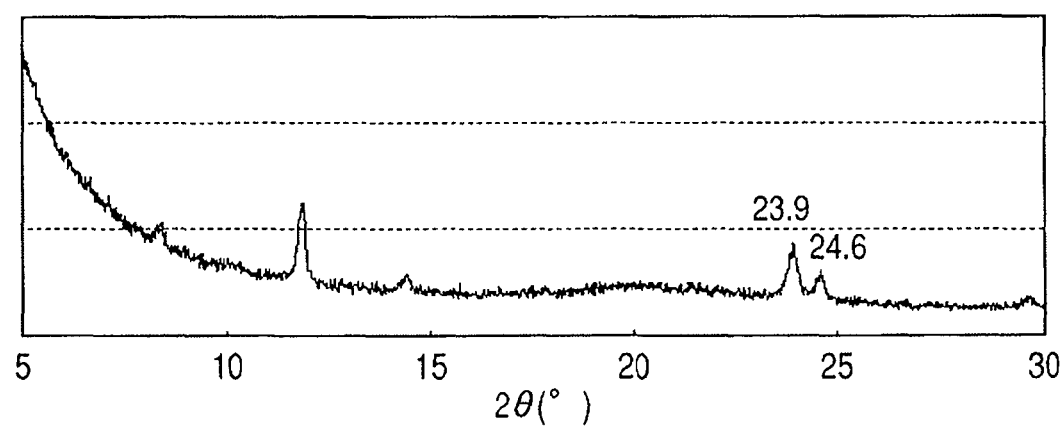
FIG. 9 is an X-ray diffraction pattern of the transistor substrate obtained in Comparative Example 1 of the present invention.

These results are shown in Table 1 and FIG. 9.

TABLE 1

|  | Mobility (cm²/Vs) | ON/OFF ratio | $I_1/I_2$ |
| --- | --- | --- | --- |
| Example 1 | $1.5 \times 10^{-1}$ | $1.2 \times 10^5$ | 13 |
| Example 2 | $5.2 \times 10^{-1}$ | $2.3 \times 10^5$ | 2.8 |
| Example 3 | $1.3 \times 10^{-1}$ | $1.6 \times 10^5$ | 2.5 |
| Comparative Example 1 | $2.3 \times 10^{-3}$ | $3.3 \times 10^2$ | <0.2 |

This application claims priority from Japanese Patent Application No. 2004-067440 filed Mar. 10, 2004, which is hereby incorporated by reference herein.

The invention claimed is:

1. A field effect transistor comprising an organic semiconductor layer, a source electrode, a drain electrode, a gate electrode and an insulating layer,
wherein the organic semiconductor layer contains a metal-free tetrabenzoporphyrin and a tetrabenzoporphyrin copper complex in a weight ratio of 1:1.

2. The field effect transistor according to claim 1, having an ON/OFF ratio of the order of $10^5$.

3. A field effect transistor comprising an organic semiconductor layer, a source electrode, a drain electrode, a gate electrode and an insulating layer,
wherein the organic semiconductor layer contains a metal-free tetrabenzoporphyrin and a tetrabenzoporphyrin copper complex and has a maximum diffraction intensity $I_1$ in a Bragg angle (2θ) range of 9.9° to 10.4° stronger than a maximum diffraction intensity $I_2$ in a Bragg angle (2θ) range of 23.0° to 26.0° in X-ray diffraction using CuKα radiation.

4. The field effect transistor according to claim 3, wherein the organic semiconductor layer contains the metal-free tetrabenzoporphyrin and the tetrabenzoporphyrin copper complex in a weight ratio of 1:1.

5. The field effect transistor according to claim 3, having an ON/OFF ratio of the order of $10^5$.

6. A field effect transistor comprising an organic semiconductor layer, a source electrode, a drain electrode, a gate electrode and an insulating layer,
wherein the organic semiconductor layer contains at least a porphyrin compound and has a maximum diffraction intensity $I_1$ in a Bragg angle (2θ) range of 9.9° to 10.4° stronger than a maximum diffraction intensity $I_2$ in a Bragg angle (2θ) range of 23.0° to 26.0° in X-ray diffraction using CuKα radiation,
the organic semiconductor layer is obtained by heating a metal-free tetrabicyclo compound, which is a precursor of the porphyrin compound and which is of the following formula

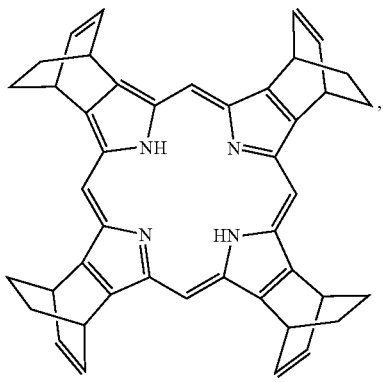

and
the organic semiconductor layer is in contact with a methyl-silsesquioxane interface layer that is arranged between the insulating layer and the organic semiconductor layer.

7. The field effect transistor according to claim 6, wherein a ratio $I_1/I_2$ of the maximum diffraction intensity $I_1$ to the maximum diffraction intensity $I_2$ is 2 or more.

8. The field effect transistor according to claim 6, having an ON/OFF ratio of the order of $10^5$.

9. A method of producing a field effect transistor comprising an organic semiconductor layer, a source electrode, a drain electrode, a gate electrode and an insulating layer, the method comprising the steps of:
providing a methyl-silsesquioxane interface layer on the insulating layer;
heating a precursor having a bicyclo[2.2.2]octadiene skeleton to form a porphyrin compound on the interface layer; and
using at least the porphyrin compound to form at least the organic semiconductor layer,
wherein the organic semiconductor layer has a maximum diffraction intensity $I_1$ in a Bragg angle (2θ) range of 9.9° to 10.4° stronger than a maximum diffraction intensity $I_2$ in a Bragg angle (2θ) range of 23.0° to 26.0° in X-ray diffraction using CuKα radiation, and
the precursor is a metal-free tetrabicyclo compound of the following formula

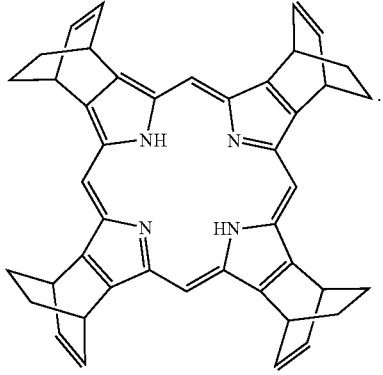

10. The method of producing a field effect transistor according to claim 9, wherein the porphyrin compound is used to form the organic semiconductor layer so that the organic semiconductor layer has a ratio $I_1/I_2$ of the maximum diffraction intensity $I_1$ to the maximum diffraction intensity $I_2$ is 2 or more.

11. The method of producing a field effect transistor according to claim 9, wherein the field effect transistor has an ON/OFF ratio of the order of $10^5$.

* * * * *